United States Patent [19]

Hayakawa et al.

[11] Patent Number: 4,990,653

[45] Date of Patent: Feb. 5, 1991

[54] SULFUR-CONTAINING ACRYL OLIGOMER COMPOSITION

[75] Inventors: Seiichiro Hayakawa; Shoji Ichihara, both of Ibaraki, Japan

[73] Assignee: Mitsubishi Petrochemical Co., Ltd., Tokyo, Japan

[21] Appl. No.: 330,809

[22] Filed: Mar. 30, 1989

[30] Foreign Application Priority Data

Apr. 4, 1988 [JP] Japan ............................... 63-82638

[51] Int. Cl.$^5$ ............................................. C07C 69/52
[52] U.S. Cl. ................................................... 560/221
[58] Field of Search ......................................... 560/221

[56] References Cited

FOREIGN PATENT DOCUMENTS 0252006 6/1987 European Pat. Off. .
3321501 12/1984 Fed. Rep. of Germany .
3431844 3/1986 Fed. Rep. of Germany .
62-195357 8/1987 Japan .

OTHER PUBLICATIONS

A Copy of the Corresponding CA108:57489u is Being Supplied for Applicants' Convenience.
Patent Abstracts of Japan, Unexamined Applications, C Field, vol. 10, No. 239, Aug. 19, 1986, The Patent Office Japanese Government, p. 109 C 367 *Kokai-No. 61-72 748 (Mitsubishi Petrochem)*.
Patent Abstracts of Japan, Unexamined Applications, C Field, vol. 12, No. 47, Feb. 12, 1988, The Patent Office Japanese Government, p. 159 C 475 *Kokai-No. 62-195 537 (Mitsubishi Petrochem)*.

*Primary Examiner*—Paul J. Killos

*Attorney, Agent, or Firm*—Oblon, Spivak, McClelland, Maier & Neustadt

[57] ABSTRACT

A sulfur-containing acryl oligomer composition represented by formula (I):

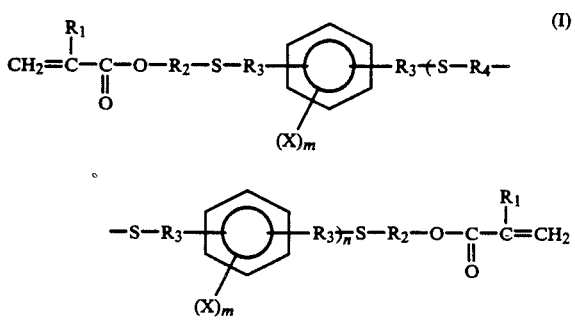

wherein $R_1$ represents a hydrogen atom or a methyl group; $R_2$ and $R_3$ each represents an alkylene group having from 1 to 12 carbon atoms; $R_4$ represents an alkylene group having from 1 to 12 carbon atoms, an oxydialkylene group having from 2 to 12 carbon atoms, or an aralkylene group having from 6 to 20 carbon atoms; X represents a chlorine, bromine or iodine atom; m represents 0 or an integer of from 1 to 4; and n represents an average degree of oligomerization of 10 or smaller.

The oligomer composition provides on polymerization a cured product having a refractive indices of 1.60 or higher, excellent transparency, and optical uniformity and is therefore useful as a material for plastic lenses.

5 Claims, No Drawings

SULFUR-CONTAINING ACRYL OLIGOMER COMPOSITION

FIELD OF THE INVENTION

This invention relates to a sulfur-containing acryl oligomer composition. More particularly, it relates to an oligomer composition which is cured with optical uniformity to provide a cured product suitable for use as a plastic lens, having a high refractive index, excellent transparency and satisfactory processability.

BACKGROUND OF THE INVENTION

Plastic lenses have advantages not possessed by inorganic glass lenses, such as lightweight, safety, processability, dyeability, and the like.

Polydiethylene glycol bis(allyl carbonate) ("CR-39", a trade name of PPG Co.) has been widespread as a material for plastic lenses because of its excellence in various characteristics but has a low refractive index $n_D$ as 1.50 and does not therefore suffice for needs of further reduction in weight and dimensions of plastic lenses.

There are several reports on polymers having increased refractive indices ($n_D$=ca. 1.60) which are obtained by using a residue of bisphenol A, etc. in a monomer skeleton as disclosed in JP-A-No. 61-72748 and JP-A-No. 62-195357 (the term "JP-A" as used herein means an "unexamined published Japanese patent application"). However, these polymers involve disadvantages fatal to use as optical lenses. That is, the casting monomer undergoes shrinkage from mold dimension on polymerization (curing), failing to obtain a desired surface shape as designed, and the cured product is liable to suffer from optical strain due to residual stress or orientation.

In order to overcome these problems on polymerization casting, it has been proposed to previously increase the density of the casting liquid before cast molding or to lengthen the distance between crosslinking points to thereby alleviate contraction. However, these techniques of using a prepolymer are not easy to actually carry out because the casting liquid is highly apt to gel on prepolymerization and difficult to control so as to have a desired viscosity. Moreover, the resulting prepolymer is unsatisfactory in storage stability.

SUMMARY OF THE INVENTION

One object of this invention is to provide a curable material capable of providing a cured product having a refractive index of 1.60 or higher, satisfactory transparency, and optical uniformity.

This invention relates to a sulfur-containing acryl oligomer composition represented by formula (I):

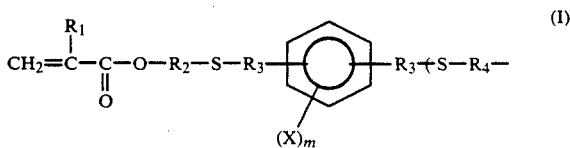

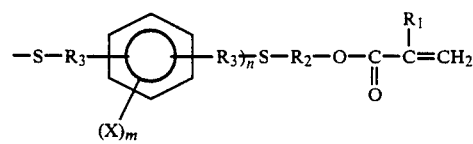

wherein $R_1$ represents a hydrogen atom or a methyl group; $R_2$ and $R_3$ each represents an alkylene group having from 1 to 12 carbon atoms; $R_4$ represents an alkylene group having from 1 to 12 carbon atoms, an oxydialkylene group having from 2 to 12 carbon atoms, or an aralkylene group having from 6 to 20 carbon atoms; X represents a chlorine, bromine or iodine atom; m represents 0 or an integer of from 1 to 4; and n represents an average degree of oligomerization of 10 or smaller.

DETAILED DESCRIPTION OF THE INVENTION

The oligomer composition according to the present invention is a mixture comprising a monomer represented by formula:

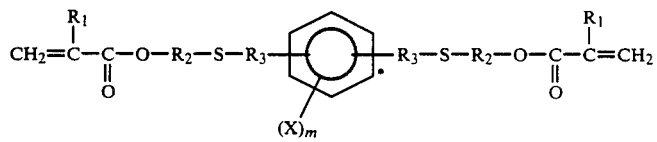

wherein $R_1$, $R_2$, $R_3$, X, and m are as defined above, and an oligomer having its chain lengthened by a group which functions to increase a refractive index, said oligomer being represented by formula:

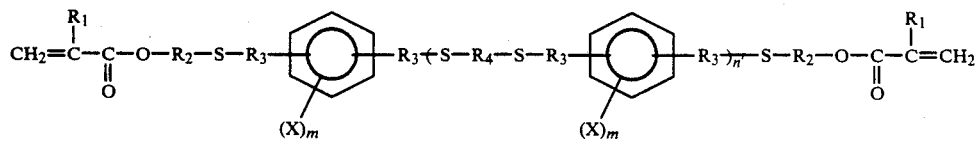

wherein $R_1$, $R_2$, $R_3$, $R_4$, X, and m are as defined above; and n' represents a number of at least 1.

The average degree of oligomerization of the oligomer composition [n in formula (I)] is 10 at the highest, preferably 5 or smaller, more preferably from 0.1 to 1, and most preferably from 0.1 to 0.5.

If the average degree of oligomerization is too small, oligomerization cannot bring any significant improvement so that the composition finds difficulty in uniformly curing and fails to obtain a sufficiently high refractive index. If it is too high, the viscosity of the composition excessively increases due to molecular weight increase, thus making handling very difficult.

In formula (I), the alkylene group as represented by $R_2$, $R_3$ or $R_4$ includes methylene, ethylene, butylene, hexylene, and octylene groups, with those containing up to 4 carbon atoms being preferred.

The oxydialkylene group as represented by $R_4$ includes oxydimethylene, methyleneoxyethylene, methylenebisoxyethylene, and oxydipropylene groups, with those containing from 2 to 6 carbon atoms being preferred. More preferred are those containing 4 carbon atoms.

The aralkylene group as represented by $R_4$ includes phenylene and xylylene groups, with those containing from 6 to 12 carbon atoms being preferred.

The oligomer composition of the present invention can be obtained by esterifying a diol-terminated oligomer composition prepared from a dihalogen compound, a dimercaptan compound, and a hydroxyl-containing mercaptan compound with acrylic acid or methacrylic acid.

Details of the production of the oligomer composition will hereinafter be described by referring to the reaction scheme illustrated below.

m-xylene, α,α'-dibromo-o-xylene, α,α'-dibromo-p-xylene, α,α'-dibromo-m-xylene, α,α'-dibromo-o-xylene, α,α', 2,3,5,6-hexachloro-p-xylene, α,α', 2,3,5,6-hexachloro-m-xylene, α,α',2,3,5,6-hexachloro-o-xylene, α,α', 2,3,5,6-hexabromo-p-xylene, α,α',2,3,5,6-hexabromo-m-xylene, α,α', 2,3,5,6-hexabromo-o-xylene, p-bis(β-chloroethyl)benzene, m-bis(β-chloroethyl)benzene, o-bis(β-chloroethyl)benzene, p-bis(β-chloroethyl)tetrachlorobenzene, m-bis(β-chloroethyl)tetrachlorobenzene, p-bis(β-bromoethyl)tetrabromobenzene, m-bis(β-bromoethyl)tetrabromobenzene, p-(6-chlorohexyl)benzene, m-bis(6-bromohexyl)benzene, p-bis(10-chlorooctyl)benzene, and m-bis(10-chlorooctyl)benzene.

Specific examples of the dimercaptan compound of formula (III) are dimercaptoethane, dimercaptopropane, dimercaptobutane, di(mercaptoethyl) ether, methylenebisoxyethanethiol, dimercaptobenzene, and α,α'-dimercapto-p-xylene.

The molar ratio of the dimercaptan compound to dihalogen compound is subject to variation according to the desired n value (average degree of oligomeriza-

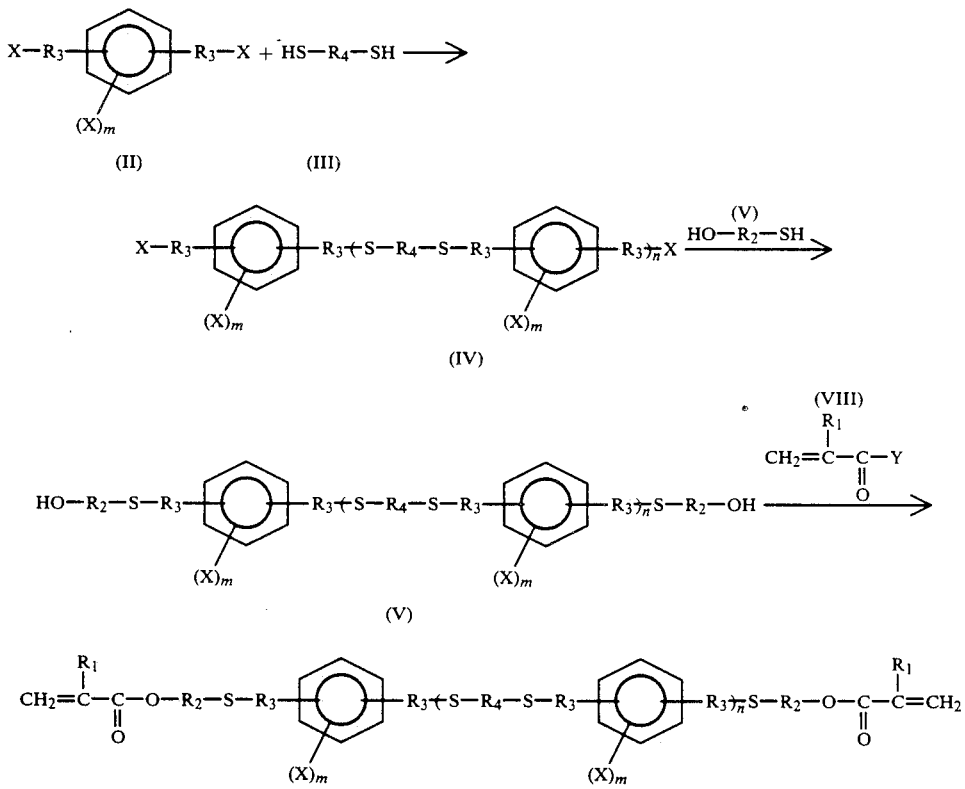

wherein $R_1$, $R_2$, $R_3$, $R_4$, X, m, and n are as defined above; and Y represents a chlorine atom, a hydroxyl group, a (meth)acryloyl residue, or an alkoxy group.

(1) Synthesis of Dihalogen-Terminated Oligomer Composition (IV):

A dihalogen compound represented by formula (II) and a dimercaptan compound represented by formula (III) are reacted at a (II)/(III) molar ratio of more than 1 in accordance with a known process as described, e.g., in Shunsuke Murahashi, *Gosei Kobunshi IV*, p. 359, to obtain a dihalogen-terminated oligomer composition represented by formula (IV).

Specific examples of the dihalogen compound of formula (II) are α,α'-dichloro-p-xylene, α,α'-dichlorotion) of the oligomer composition. More specifically, the mercaptan compound is used in an amount of from 0.09 mol to 0.91 mol per mol of the dihalogen compound to obtain an oligomer composition wherein n is from 0.1 to 10, respectively, and preferably in an amount of from 0.09 to 0.5 mol per mol of the dihalogen compound to obtain an oligomer composition wherein n is from 0.1 to 1, respectively.

The reaction can be carried out in a solvent, such as water, alcohols (e.g., methanol, ethanol, (iso)propyl alcohol), ketones (e.g., methyl ethyl ketone, acetone), or halogen solvents (e.g., methylene chloride, chloroform), or a mixed solvent of water and these organic solvents. The amount of the solvent to be used ranges from 500 to 1,000 ml per mol of the dihalogen compound. In case of using a mixed solvent, the water to organic solvent volume ratio is up to 100, preferably up to 1. The reaction is effected at a temperature of from 50° to 100° C., preferably from 70° to 90° C. In the reaction, a metal salt, e.g., potassium carbonate and sodium hydroxide, is used as a neutralizing agent in an amount equivalent to the dimercaptan compound or in excess.

The reaction may be performed by first reacting the dimercaptan compound with the metal salt (e.g., potassium carbonate, sodium hydroxide) in the solvent to once form a dimercaptan metal salt, which is then reacted with the dihalogen compound.

After completion of the reaction, the solvent is removed by distillation, and the residue is washed with water and dried to obtain a dihalogen-terminated oligomer composition. The composition and the total mole number of the resulting oligomer composition depend on the molar ratio of the reactants and can be determined by liquid chromatography or by use of molecular weight distribution measuring equipment.

(2) Synthesis of Diol-Terminated Oligomer Composition (VI):

The dihalogen-terminated oligomer composition as obtained in (1) above is reacted with a haydroxyl-containing mercaptan compound represented by formula (V) according to a known process as described, e.g., in N, Kharasch, *Organic Sulfur Compounds*, Vol. 1, Ch. 11, pp. 97–111 or U.S. Pat. No. 3,824,293, to obtain a diol-terminated oligomer composition represented by formula (VI).

Specific examples of the hydroxyl-containing mercaptan compound are 2-mercaptoethanol, 3-mercaptopropanol, 2-mercapto-1-methylethanol, and 6-mercaptohexanol.

The hydroxyl-containing mercaptan compound is usually used in an amount double the molar quantity of the dihalogen-terminated oligomer composition or in slight excess. The reaction can be carried out in a solvent selected from those enumerated above for use in the preparation of the dihalogen-terminated oligomer composition. The reaction temperature ranges usually from 50° to 110° C., preferably 70° to 90° C. A metal salt such as potassium carbonate and sodium hydroxide is used as a neutralizing agent in an amount half the molar quantity of the hydroxyl-containing mercaptan compound or in excess.

While the aforesaid metal salt is used to neutralize hydrochloric acid produced, the reaction may be effected by first reacting the hydroxyl-containing mercaptan compound with the metal salt in the solvent to once synthesize a metal salt of the hydroxyl-containing mercaptan compound, which is then reacted with the dihalogen-terminated oligomer composition.

After the reaction, the solvent is removed by distillation, and the residue is washed with water and dried to obtain the diol-terminated oligomer composition of formula (VI).

It is possible to perform the above-described reaction by using the dihalogen-terminated oligomer composition as produced by the reaction of (1) above without isolation. Such being the case, adequate amounts of the hydroxyl-containing mercaptan compound and the metal salt (e.g., potassium carbonate, sodium hydroxide) are added to the reaction system containing the dihalogen-terminated oligomer composition produced to thereby effect the reaction successively. Instead of adding the metal salt here, the metal salt in an amount as required for both the reaction between the dihalogen compound and the dimercaptan compound and the subsequent reaction with the hydroxyl-containing mercaptan compound may be added to the former reaction system from the first. Further, it is also possible to start with a system containing the three reactants, i.e., dihalogen compound, dimercaptan compound, and a hydroxyl-containing mercaptan compound, in such a mixing ratio as to obtain a desired n value.

The composition, the total mole number and the like of the resulting diol-terminated oligomer composition can be determined by liquid chromatography or by use of molecular weight distribution measuring equipment.

(3) Synthesis of Sulfur Containing Acryl Oligomer Composition (I):

The diol-terminated oligomer composition as obtained in (2) above is reacted with an acylating agent represented by formula (VII) to obtain a sulfur-containing acryl oligomer composition according to the present invention.

Specific examples of the acylating agent to be used include carboxylic acids and halides, esters or anhydroxides thereof, e.g., (meth)acrylic acid, (meth)acrylic acid chloride, (meth)acrylic acid bromide, methyl (meth)acrylate, ethyl (meth)acrylate, and (meth)acrylic anhydride. The term "(meth)acrylic" or "(meth)acrylate" is used here to cover both acrylic or acrylate and methacrylic or methacrylate.

In the case of using a carboxylic acid as an acylating agent, a catalyst, such as mineral acids (e.g., sulfuric acid, hydrochloric acid) and aromatic sulfonic acids (e.g., p-toluenesulfonic acid), is used in an amount of from 0.01 to 0.5 mol per mol of the diol-terminated oligomer composition, and (meth)acrylic acid is used in an amount of from 2 to 6 mols, preferably from 2 to 3 mols, per mol of the oligomer composition. The reaction can be conducted in 500 to 1,000 ml, per mol of the diol-terminated oligomer composition, of a solvent, such as benzene and toluene, at a temperature of from 60° to 120° C., preferably from 80° to 110° C., while azeotropically removing water produced.

In the case of using a carboxylic acid ester as an acylating agent, a catalyst, such as organic metal complexes (e.g., titanium butoxide, potassium butoxide), is used in an amount of from 0.01 to 0.5 mol per mol of the diol-terminated oligomer composition, and methyl (meth)acrylate is used in an amount of from 2 to 6 mols, preferably from 2 to 3 mols, per mol of the diol-terminated oligomer composition. The reaction can be carried out in the presence or absence of a solvent at a temperature of from 60° to 120° C., preferably from 80° to 110° C., while azeotropically removing the alcohol produced.

In the case of using a (meth)acrylic anhydride as an acylating agent, the reaction can be effected in the same manner as for the case of using the carboxylic acid ester. The produced carboxylic acid is removed from the reaction system after completion of the reaction.

In the case of using an acid halide as an acylating agent, the reaction can be carried out in the presence of from 2 to 6 mols, preferably from 2 to 3 mols, of a nitrogen-containing organic base (e.g., triethylamine, tributylamine, diisopropylamine, pyridine) per mole of the diol-terminated oligomer composition. The reaction is effected by dropwise addition of the acid halide while maintaining the system comprising the diol-terminated oligomer composition and the nitrogen-containing organic base at a temperature within a range of from −10° C. to 50° C., preferably from −10° C. to 30° C. A solvent may or may not be used, but it is preferable to use an inert solvent, such as ketones (e.g., acetone, methyl ethyl ketone), chlorinated solvents (e.g., chloroform, dichloromethane), and ethers (e.g., tetrahydrofuran, dioxane).

In any of the above-described cases, the reaction mixture is washed successively with dilute hydrochloric acid, a dilute alkali aqueous solution, and water. The solvent, if used, is then removed therefrom by distillation to thereby obtain the sulfur-containing (meth)acryl oligomer composition of the invention.

In the present invention, the n value of the oligomer composition may also be controlled by addition of monomers or blending of oligomers having different n values.

The sulfur-containing (meth)acryl oligomer composition according to the present invention can be cured by polymerization in the presence of a radical polymerization initiator to provide a cured product having a refractive index of 1.60 or higher, satisfactory transparency, and optical uniformity. The oligomer composition may also be copolymerized with other radical polymerizable comonomers. Such comonomers include vinyl compounds, e.g., styrene, vinyltoluene, methoxystyrene, chlorostyrene, bromostyrene, dichlorostyrene, dibromostyrene, trichlorostyrene, divinylbenzene, vinylnaphthalene, vinyl acetate, and vinyl chloride; (meth)acrylates, e.g., methyl methacrylate, phenyl methacrylate, phenyl acrylate, chlorophenyl methacrylate, bromophenyl methacrylate, benzyl methacrylate, 2-hydroxyethylmethacrylate, glycidiyl methacrylate, trimethylolpropane triacrylate, and epoxy acrylate; and allyl compounds, e.g., diethylene glycol bis(allyl carbonate), diallyl phthalate, diallyl epoxysuccinate, allylphenylsilane, and diallyldimethylsilane.

The radical initiator which can be used for polymerization is not particularly limited, and those commonly employed in the art can be used. Specific examples of useful initiators are peroxides, e.g., benzoyl peroxide, diisopropyl peroxycarbonate, t-butyl peroxyisopropylcarbonate, and di-t-butyl peroxide; azo compounds, e.g., azobisisobutylonitrile; photosensitizers, e.g., benzophenone, benzoin, benzoin ethyl ether, benzylacetophenone, anthracene, and α-chloromethylnaphthalene; and sulfur compounds, e.g., diphenyl sulfide, and thiocarbamate.

The present invention is now illustrated in greater detail by way of Preparation Examples, Examples, Application Examples, and Comparative Example, but it should be understood that the present invention is not deemed to be limited thereto. In these examples, all the parts are given by weight unless otherwise indicated.

PREPARATION EXAMPLE 1

In a 1,000 ml-volume four-necked flask equipped with a stirrer, a thermometer, a dropping funnel, and a condenser were charged 100 parts of α,α'-dichloro-p-xylene, 9 parts of dimercaptoethane, 95 parts of potassium carbonate, and 500 parts of methyl ethyl ketone. The solution was heated to 82° to 83° C. while stirring, followed by refluxing for 3 hours. Then, 82 parts of 2-mercaptoethanol was added dropwise to the solution while stirring, followed by refluxing for 3 hours. After completion of the reaction, the solvent was removed by distillation, and the residue was washed with water and dried in warm air to obtain 156 parts (94%) of a sulfur-containing diol-terminated oligomer composition having formula shown below as a white powder.

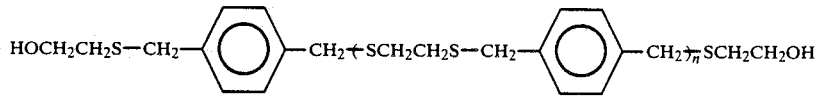

The resulting oligomer composition was found to have an n value of 0.20 by high performance liquid chromatography.

PREPARATION EXAMPLES 2 TO 8

In the same manner as described in Preparation Example 1, except for changing the weight ratio of the reactants as shown in Table 1 below, sulfur-containing diol-terminated oligomer compositions shown in Table 1 were obtained.

TABLE 1

| Preparation Example No. | Reactants — Dihalogen Compound | Reactants — Dimercaptan Compound | $K_2CO_3$ | Diol-Terminated Oligomer Composition $HOCH_2CH_2S-R-SCH_2CH_2OH$ | n |
|---|---|---|---|---|---|
| 1 | ClCH$_2$–C$_6$H$_4$–CH$_2$Cl (para), 100 parts | HSCH$_2$CH$_2$SH | 9 parts | 95 parts | $R = -CH_2-C_6H_4-CH_2(-SCH_2CH_2S-CH_2-C_6H_4-CH_2)_n$ | 0 |
| 2 | ClCH$_2$–C$_6$H$_4$–CH$_2$Cl (para), 100 parts | HSCH$_2$CH$_2$SH | 12 parts | 93 parts | $R = -CH_2-C_6H_4-CH_2(-SCH_2CH_2S-CH_2-C_6H_4-CH_2)_n$ | 0 |
| 3 | ClCH$_2$–C$_6$H$_4$–CH$_2$Cl (meta), 100 parts | HSCH$_2$CH$_2$SH | 12 parts | 93 parts | $R = -CH_2-C_6H_4-CH_2(-SCH_2CH_2S-CH_2-C_6H_4-CH_2)_n$ | 0 |
| 4 | ClCH$_2$–C$_6$H$_4$–CH$_2$Cl (para), 100 parts | HSCH$_2$CH$_2$OCH$_2$CH$_2$SH | 18 parts | 86 parts | $R = -CH_2-C_6H_4-CH_2(-SCH_2CH_2OCH_2CH_2S-CH_2-C_6H_4-CH_2)_n$ | 0 |
| 5 | ClCH$_2$–C$_6$H$_4$–CH$_2$Cl (para), 100 parts | HSCH$_2$CH$_2$OCH$_2$CH$_2$SH | 23 parts | 87 parts | $R = -CH_2-C_6H_4-CH_2(-SCH_2CH_2OCH_2CH_2S-CH_2-C_6H_4-CH_2)_n$ | 0 |
| 6 | ClCH$_2$–C$_6$Cl$_4$–CH$_2$Cl (tetrachloro), 100 parts | HSCH$_2$CH$_2$OCH$_2$CH$_2$SH | 7 parts | 53 parts | $R = -CH_2-C_6Cl_4-CH_2(-SCH_2CH_2OCH_2CH_2S-CH_2-C_6H_4-CH_2)_n$ | 0 |

TABLE 1-continued

| Preparation Example No. | Reactants | | | Diol-Terminated Oligomer Composition $HOCH_2CH_2S-R-SCH_2CH_2OH$ | n |
| --- | --- | --- | --- | --- | --- |
| | Dihalogen Compound | Dimercaptan Compound | $K_2CO_3$ | | |
| 7 | ClCH$_2$—⟨C$_6$H$_4$⟩—CH$_2$Cl<br>100 parts | HS—⟨C$_6$H$_4$⟩—SH<br>14 parts | 95 parts | $R = -CH_2-$⟨C$_6$H$_4$⟩$-CH_2-(S-CH_2-$⟨C$_6$H$_4$⟩$-S-CH_2-$⟨C$_6$H$_4$⟩$-CH_2-)_n$ | 0 |
| 8 | ClCH$_2$—⟨C$_6$H$_4$⟩—CH$_2$Cl<br>100 parts | HSCH$_2$—⟨C$_6$H$_4$⟩—CH$_2$SH<br>16 parts | 95 parts | $R = -CH_2-$⟨C$_6$H$_4$⟩$-CH_2-(S-CH_2-$⟨C$_6$H$_4$⟩$-CH_2-S-CH_2-$⟨C$_6$H$_4$⟩$-CH_2-)_n$ | 0 |

EXAMPLE 1

In a 1,000 ml-volume four-necked flask equipped with a stirrer, a thermometer, and a condenser-connecting separator were charged 156 parts of the sulfur-containing diol-terminated oligomer composition as obtained in Preparation Example 1, 100 parts of methyl methacrylate, and 0.3 part of p-methoxyphenol as a polymerization inhibitor. After the mixture was heated up to 80° C. while stirring, 4 parts of titanium butoxide was added thereto to effect interesterification. The produced methanol was removed out of the system as an azeotropic mixture with methyl methacrylate. The reaction mixture was transferred to a separatory funnel, and 300 parts of toluene was added thereto. The reaction mixture was washed successively with dilute hydrochloric acid and a dilute alkali aqueous solution and then washed with water until the washing became neutral. The mixture was dehydrated over anhydrous magnesium sulfate, filtered, and distilled under reduced pressure to remove toluene to obtain 215 parts (88%) of a sulfur-containing dimethacrylate oligomer composition having formula shown below, wherein n was 0.2, as a colorless transparent liquid.

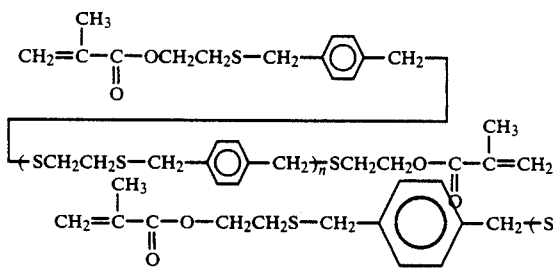

EXAMPLE 2

In the same manner as in Example 1, except for replacing the diol-terminated oligomer composition as used in Example 1 with 164 parts of the diol-terminated oligomer composition as obtained in Preparation Example 2, 215 parts (88%) of a sulfur-containing dimethacrylate oligomer composition having formula shown below, wherein n was 0.3, was obtained.

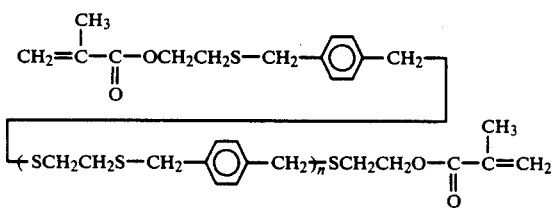

The product was a white lardaceous solid and became a colorless transparent liquid on heating to 60° C.

EXAMPLE 3

In the same manner as in Example 2, except for using 167 parts of the diol-terminated oligomer composition as obtained in Preparation Example 3, 205 parts (82%) of a sulfur-containing dimethacrylate oligomer composition having formula shown below, wherein n was 0.3, was obtained as a colorless transparent liquid.

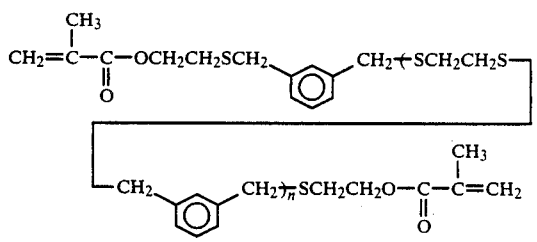

EXAMPLE 4

In the same manner as in Example 2, except for using 175 parts of the diol-terminated oligomer composition as obtained in Preparation Example 4, 218 parts (85%) of a sulfur-containing dimethacrylate oligomer composition having formula shown below, wherein n was 0.3, was obtained as a colorless transparent liquid.

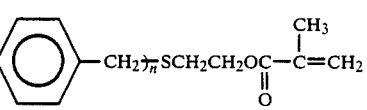

EXAMPLE 5

In the same manner as in Example 2, except for using 176 parts of the diol-terminated oligomer composition as obtained in Preparation Example 5, 241 parts (91%) of a sulfur-containing dimethacrylate oligomer composition having formula shown below, wherein n was 0.4, was obtained as a colorless transparent liquid.

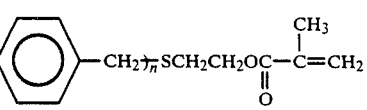

EXAMPLE 6

In the same manner as in Example 2, except for using 118 parts of the diol-terminated oligomer composition as obtained in Preparation Example 6, 148 parts (82%) of a sulfur-containing dimethacrylate oligomer composition having formula shown below, wherein n was 0.2, was obtained as a colorless transparent liquid.

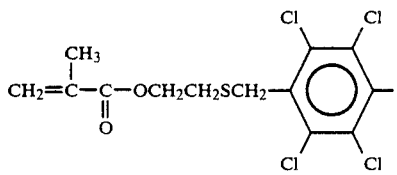 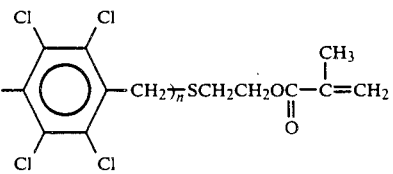

EXAMPLE 7

In the same manner as in Example 2, except for using 141 parts of the diol-terminated oligomer composition as obtained in Preparation Example 7, 189 parts (76%) of a sulfur-containing dimethacrylate oligomer composition having formula shown below, wherein n was 0.2, was obtained.

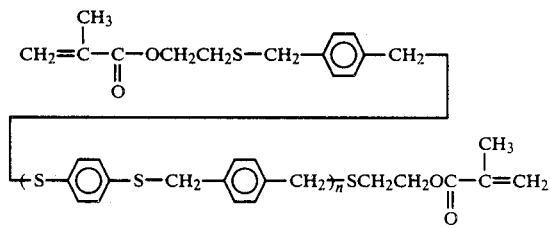

The product was a white lardaceous solid at room temperature but became a colorless transparent liquid on heating to 70° C.

EXAMPLE 8

In the same manner as in Example 2, except for using 172 parts of the diol-terminated oligomer composition as obtained in Preparation Example 8, 232 parts (89%) of a sulfur-containing dimethacrylate oligomer composition having formula shown below, wherein n was 0.2, was obtained.

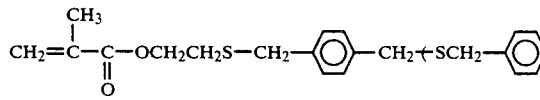

The product was a white lardaceous solid at room temperature but became a colorless transparent liquid on heating to 50° C.

APPLICATION EXAMPLE 1

A mixture consisting of 100 parts of the sulfur-containing dimethacrylate oligomer composition as obtained in Example 1 and 0.5 part of benzoyl peroxide was cast in a mold composed of a glass mold for lens forming and a gasket made of a silicone rubber, and the temperature was elevated to 60° C. up to 110° C. over a period of 12 hours to effect polymerization. The lens removed from the mold was satisfactory in both light transmission properties and hardness.

APPLICATION EXAMPLES 2 TO 8

Each of the sulfur-containing dimethacrylate oligomer compositions obtained in Examples 2 to 8 was polymerized and cured in the same manner as in Application Example 1. The resulting lenses were all proved satisfactory in both light transmission properties and hardness.

COMPARATIVE EXAMPLE p-Bis($\beta$-methacryloyloxyethylthio)xylylene having formula shown below was polymerized and cured in the same manner as in Application Example 1.

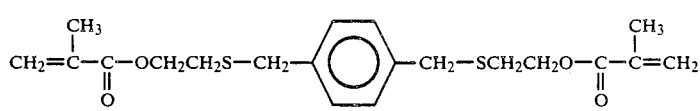

The specific gravity (dp), refractive index ($n_D$), Abbe's number ($\nu_D$), and percent of contraction of the cured products obtained in Application Examples 1 to 8 and Comparative Example were measured. The percent contraction was obtained from equation:

Percent Contraction (%) = (1 − dm/dp) × 100 wherein dm is a specific gravity of the monomer; and dp is a specific gravity of the polymer.

Further, the curing state, i.e., optical strain of the cured products was observed visually and also with a polarimeter and rated as follows:

| Excellent | No optical strain was observed. |
|---|---|
| Good | No substantial optical strain was observed. |
| Poor | Optical strain was observed. |

The results of these measurements and observation are shown in Table 2.

TABLE 2

| Application Example No. | Casting Material | dp | $n_D$ | $\nu_D$ | Percent Contraction (%) | Curing State |
|---|---|---|---|---|---|---|
| 1 | Oligomer Composition of Example 1 | 1.25 | 1.60 | 35 | 12 | good |
| 2 | Oligomer Composition of Example 2 | 1.24 | 1.61 | 34 | 11 | good |
| 3 | Oligomer Composition of Example 3 | 1.24 | 1.61 | 34 | 11 | excellent |

TABLE 2-continued

| Application Example No. | Casting Material | dp | $n_D$ | $\nu_D$ | Percent Contraction (%) | Curing State |
| --- | --- | --- | --- | --- | --- | --- |
| 4 | Oligomer Composition of Example 4 | 1.24 | 1.60 | 35 | 11 | good |
| 5 | Oligomer COmposition of Example 5 | 1.23 | 1.61 | 34 | 10 | excellent |
| 6 | Oligomer Composition of Example 6 | 1.46 | 1.63 | 34 | 13 | good |
| 7 | Oligomer Composition of Example 7 | 1.25 | 1.62 | 35 | 13 | good |
| 8 | Oligomer Composition of Example 8 | 1.24 | 1.60 | 32 | 13 | good |
| Comparartive Example | p-Bis($\beta$-methacryloyloxy-ethylthio)eylylene | 1.25 | 1.59 | 36 | 14 | poor |

While the invention has been described in detail and with reference to specific embodiments thereof, it will be apparent to one skilled in the art that various changes and modifications can be made therein without departing from the spirit and scope thereof.

What is claimed is:

1. A sulfur-containing acryl oligomer composition represented by formula (I):

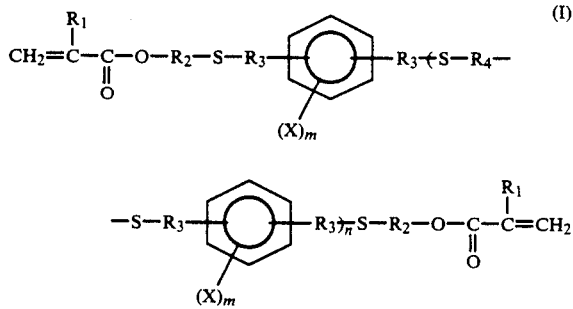

wherein $R_1$ represents a hydrogen atom or a methyl group; $R_2$ and $R_3$ each represents an alkylene group having from 1 to 12 carbon atoms; $R_4$ represents an alkylene group having from 1 to 12 carbon atoms, an oxydialkylene group having from 2 to 12 carbon atoms, or an aralkylene group having from 6 to 20 carbon atoms; X represents a chlorine, bromine or iodine atom; m represents 0 or an integer of from 1 to 4; and n represents an average degree of oligomerization of greater than 0 up to 10 inclusive.

2. A sulfur-containing acryl oligomer composition as claimed in claim 1, wherein $R_2$ and $R_3$ each represents an alkylene group having from 1 to 4 carbon atoms; $R_4$ represents an alkylene group having from 1 to 4 carbon atoms, an oxydialkylene group having from 2 to 6 carbon atoms, or an aralkylene group having from 6 to 12 carbon atoms.

3. A sulfur-containing acryl oligomer composition as claimed in claim 1, wherein n is 5 or smaller.

4. A sulfur-containing acryl oligomer composition as claimed in claim 1, wherein n is from 0.1 to 1.

5. A sulfur-containing acryl oligomer composition as claimed in claim 1, wherein n is from 0.1 to 0.5.

* * * * *